United States Patent [19]

De Luca et al.

[11] 4,269,777
[45] May 26, 1981

[54] ISOTOPICALLY LABELED VITAMIN D DERIVATIVES AND PROCESSES FOR PREPARING SAME

[75] Inventors: Hector F. De Luca; Heinrich K. Schnoes, both of Madison, Wis.; Joseph L. Napoli, Dallas, Tex.; Mary A. Fivizzani, Madison, Wis.

[73] Assignee: Wisconsin Alumni Research Foundation, Madison, Wis.

[21] Appl. No.: 41,080

[22] Filed: May 21, 1979

[51] Int. Cl.³ .............................................. C07J 9/00
[52] U.S. Cl. .............................. 260/397.1; 260/397.2; 260/239.55 R; 260/239.5; 424/236; 560/116
[58] Field of Search ......................... 260/397.2, 397.1; 560/116

[56] References Cited

U.S. PATENT DOCUMENTS 4,119,647 10/1978 Liebman ........................... 260/397.2

Primary Examiner—Elbert L. Roberts
Attorney, Agent, or Firm—Howard W. Bremer

[57] ABSTRACT

This invention relates to isotopically labeled vitamin D compounds, including radiolabeled vitamin D compounds of high specific activity, methods for their preparation, and novel intermediates in their synthesis.

The radiolabeled vitamin D compounds are characterized by high specific activity (up to 160 Ci/mmol) with the process providing a facile and convenient method for synthesizing such compounds.

23 Claims, No Drawings

ISOTOPICALLY LABELED VITAMIN D DERIVATIVES AND PROCESSES FOR PREPARING SAME

The invention described herein was made in the course of work under a grant or award from the Department of Health, Education, and Welfare.

DESCRIPTION

1. Technical Field

This invention relates to isotopically labeled vitamin D derivatives.

More specifically this invention relates to radiolabeled vitamin D derivatives having high specific activity and to vitamin D compounds labeled with the stable heavy isotopes of carbon and hydrogen.

Vitamin $D_3$ is a well-known agent for the control of calcium and phosphorous homeostasis. In the normal animal or human this compound is known to stimulate intestinal calcium transport and bone-calcium mobilization and is effective in preventing rickets.

It is also now well known that to be effective vitamin $D_3$ must be converted in vivo to its hydroxylated forms. For example, the vitamin is first hydroxylated in the liver to form 25-hydroxy vitamin $D_3$ and is further hydroxylated in the kidney to produce 1α,25-dihydroxy vitamin $D_3$ or 24,25-dihydroxy vitamin $D_3$. The 1α-hydroxylated form of the vitamin is generally considered to be the physiologically active or hormonal form of the vitamin and to be responsible for what are termed the vitamin D-like activities, such as increasing intestinal absorption of calcium and phosphate, mobilizing bone mineral, and retaining calcium in the kidneys.

2. Background Art

Essential to the establishment of the above mentioned facts was the availability of a variety of radiolabeled vitamin D derivatives (see, for example, Suda et al., *Anal. Biochem.* 43, 139 (1971), Neville and DeLuca, *Biochemistry,* 5, 2201 (1966), Jones et al., *Biochemistry* 14, 1250 (1975), Bell and Scott, *J. Label. compds.* 9, 339 (1973), DeLuca et al., *Arch. Biochem. Biophys.* 124, 122 (1968), and Yamada et al., *Anal Biochem.* 85, 34 (1978)). However, such radiolabeled compounds were either of low specific activity (0.2 to 10.6 Ci/mmol) and or/-required cumbersome syntheses.

DISCLOSURE OF INVENTION

This invention relates to isotopically labeled vitamin D compounds and specifically to certain radiolabeled vitamin D derivatives (radiotracers) characterized by very high specific activity and to an efficient and versatile method for synthesizing such compounds.

More particularly, this invention relates to the 26,27-radiolabeled derivatives of 25-hydroxycholecalciferol (25-OH-$D_3$) and 1α,25-dihydroxycholecalciferol (1α,25-(OH)$_2D_3$) and to the 24-hydroxy analogs of these compounds characterized by specific activities of up to 160 Ci/mmol.

The process of this invention offers a number of advantages:

1. introduction of the desired isotope as the last step of the synthesis with the radionuclides;
2. the avoidance of the uncertainty, unreliability and the great practical difficulties and danger inherent in the manipulation of radionuclides through a multistep chemical synthesis;
3. the production of radiolabeled compounds having very high specific activity;
4. the introduction of any isotope of carbon or hydrogen, e.g. $^{13}C$, $^{14}C$ and $^4H$ and $^3H$, can be readily accomplished.

The radiolabeled vitamin D derivatives of this invention find ready application in the determination of vitamin D metabolite levels in the blood and tissues of man and animals and can therefore be of inestimable value in determining the presence or absence of disease states, such as, osteomalacia, osteodystrophy and hyperparathyroidism. For example, such compounds are useful in known assays for 25-OH-$D_3$ (Bayard et al., *Europ. J. Clin. Invest.* 2, 195 (1972), Belsey et al., *J. Clin. Endocrinol. Metab.* 33, 554 (1971), Bouilon et al., *Clin. Chem.* 22, 364 (1976), Edelstein et al., *Clin. Sci. Mol. Med.* 46, 231 (1974), Eisman et al., *Anal. Biochem.* 80, 298 (1977), Garcia-Pascual et al., *Clin. Chim. Acta* 68, 99 (1976), Haddad and Chyu, *J. Clin. Endocrinol, Metab.* 33, 992 (1971), Haddad et al., *J. Clin. Endocrinol. Metab.* 43, 86 (1976), Jones, *Clin. Chem.* 24, 287 (1978), and Preece et al., *Clin. Chem. Acta* 54, 235 (1974)), or for 1α,25-(OH)$_2D_3$ (Brumbaugh et al., *Science* 183, 1089 (1974), Eisman et al., *Arch. Biochem. Biophys.* 176, 235 (1976), and Clemens et al., *Clin. Science Mol. Med.* 54, 329 (1978)) or for multiple assays for both 25-OH-$D_3$ and 1,25-(OH$_2D_3$ as well as other metabolites (Caldas et al., *J. Lab. Clin. Med.* 91, 840 (1978), Hughes et al., *J. Clin. Invest.* 58, 61 (1970)), or in the continued investigations of vitamin D function, binding-protein studies, target-tissue receptor isolation and characterization, autoradiographic studies, and further investigations into vitamin D metabolism.

Vitamin D compounds labeled with stable heavy isotopes of carbon or hydrogen ($^{13}C$ or $^2H$) are also useful for metabolite analysis in blood and tissues especially by mass spectrometric methods as shown by Bjorkhem and Holmberg, *Clin. Chim. Acta* 68, 215 (1976)).

Preferred compounds of this invention are radiolabeled vitamin D compounds having the following general structures:

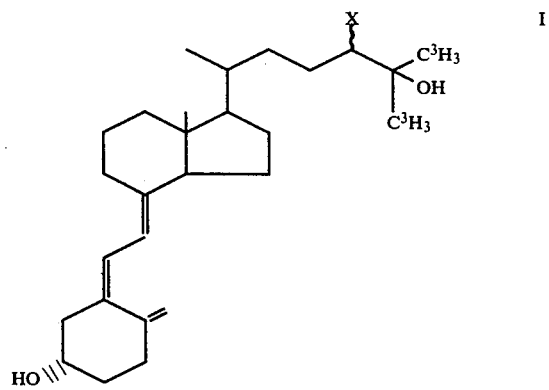

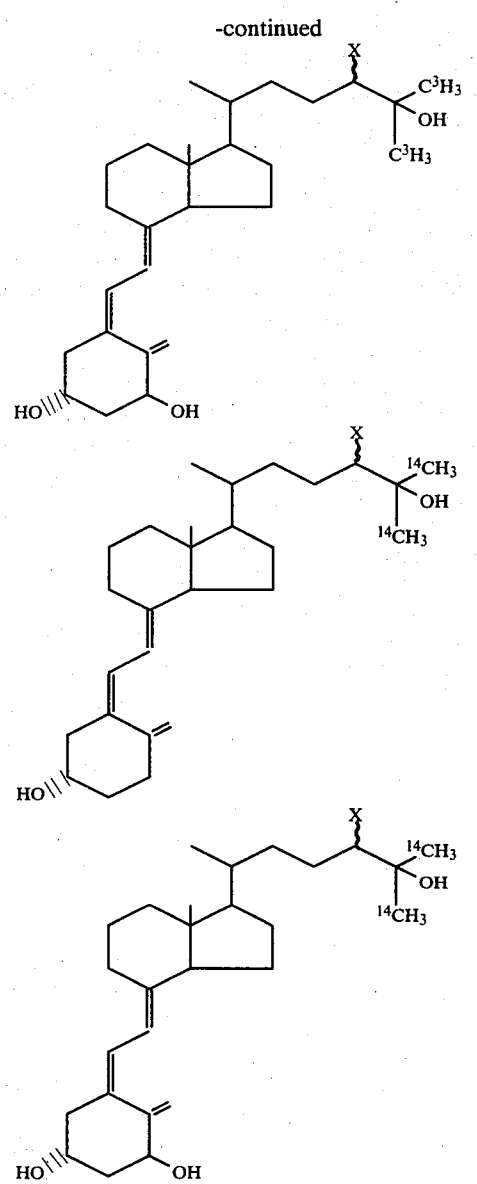

where X is selected from the group consisting of hydrogen, hydroxy, alkyl, O-alkyl, or O-acyl, and where the substituent X may have both the R and S stereochemical configuration. In all cases in this specification and in the claims the term "alkyl" refers to a lower alkyl group having from about 1 to about 4 carbon atoms, such as methyl, ethyl, propyl, isopropyl, butyl, sec. butyl, isobutyl, tert. butyl, and the term "acyl" implies either a lower aliphatic acyl group, having from about 1 to about 4 carbon atoms, such as formyl, acetyl, propionyl, butyryl, or an aromatic acyl group such as benzoyl or nitrobenzoyl.

It is also to be understood that, although the above formulae are drawn to represent the inclusion of tritium or carbon-14 as the heavy isotopes, such compounds where deuterium and carbon-13 have been substituted for the tritium and carbon-14 are also highly desirable.

BEST MODE FOR CARRYING OUT THE INVENTION

The isotopically labeled compounds of this invention are readily prepared by a process which involves treatment of an ester of 24-X-26,27-dinor-vitamin D-25-carboxylic acid (X having the designation given above), or an ester of 1α-hydroxy-24-X-26,27-dinor-vitamin D-25-carboxylic acid, with a Grignard reagent such as $C^3H_3MgBr$ or $^{14}CH_3MgBr$, or other alkyl metals such as $C^3H_3Li$ or $^{14}CH_3Li$, or the analogous deuterated or $^{13}C$-labeled Grignard or methyl lithium reagents. Examples of substrates are V, VI, VII and VIII below, where R represents an alkyl group having from about 1 to about 4 carbon atoms:

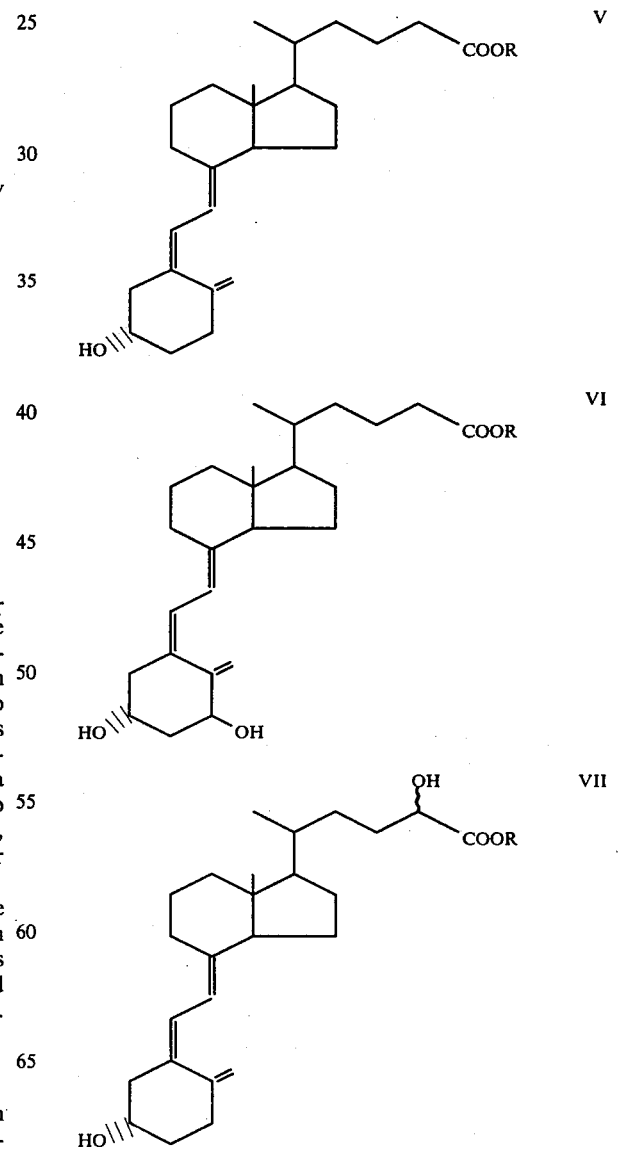

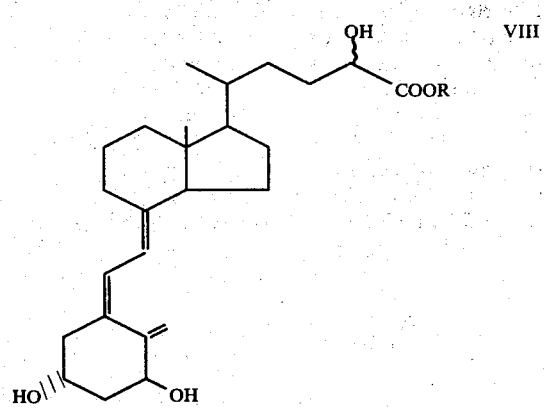

The production of isotopically labeled compounds of structures I–IV thus comprises two phases: the synthesis of appropriate unlabeled starting materials, e.g. the vitamin D compounds of type V to VIII, followed by the introduction of the desired isotopic labeled at the 26 and 27 positions.

The required vitamin D compounds V–VIII can be prepared from starting materials such as the esters of homocholenic acid or hydroxy-substituted homocholenic acid esters according to the general scheme shown in process schematic I.

Process Schematic 1

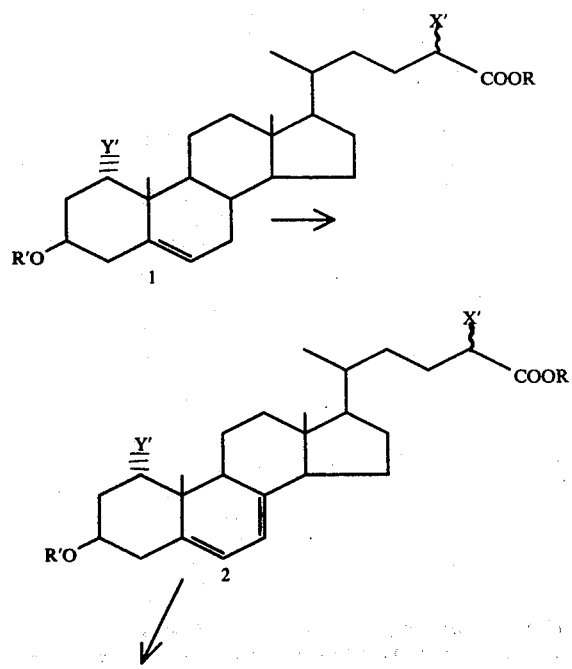

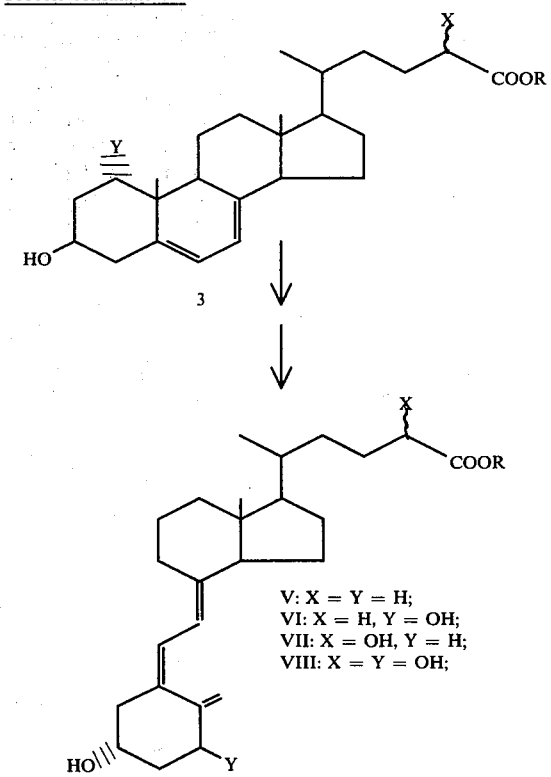

V: X = Y = H;
VI: X = H, Y = OH;
VII: X = OH, Y = H;
VIII: X = Y = OH;

In the formulae shown in the foregoing schematic, R represents a hydrocarbon radical of from 1 to about 4 carbons, $R^1$ is an alcohol protecting group such as an acyl group (e.g. acetyl or benzoyl), X and Y each may be hydrogen or hydroxyl, and $X^1$ and $Y^1$ each may be hydrogen or O-acyl. Preparation of compounds V–VIII then involves the conversion of the acyl-protected homocholenic acid ester (1) (itself generated by acylation of free hydroxy groups, by well-known acylation procedures, e.g. treatment with acetic anyhdride/pyridine, or benzoyl chloride/pyridine) to the corresponding 5,7-diene (2) using, for example, the dehydrogenation procedure of Hunzicker and Me,uml/u/ llner (Helv. Chim. Acta 61, 70 (1958)). Subsequent removal of the acyl protecting groups by hydrolysis in mild alkali yields the hydroxy ester 3. This diene is converted to the desired vitamin D product by the well-known procedure, by irradiating it with ultraviolet light, to yield the previtamin D intermediate which is then thermally isomerized to the vitamin D ester (V to VIII). These conversions are well-known in the art (see, for example, U.S. Pat. Nos. 3,907,843, 3,741,996 and 3,772,361). Alternatively, the acyl-protected 5,7-diene intermediate of structure 2, can, of course, be irradiated directly to yield the acylated previtamin D ester intermediate, which is then thermally isomerized (i.e. heating to 80°–90° C. in the presence of mild base (e.g. 10% KOH/methanol)) to effect both conversion to the vitamin 5,6-cis-triene structure and removal of the acyl groups to produce the products of structure V–VIII.

The preparation of the vitamin D ester, V, can be accomplished by direct application of the scheme above to homocholenic acid esters or 3-O-acyl derivatives thereof (e.g. structure 1 above, where R is methyl, $R^1$ is benzoyl, $X^1$ is hydrogen) which are known compounds (see, for example, Campbell et al., Steroids 13, 567–577 (1969)).

The vitamin D esters of structures VI–VII can be similarly prepared by the application of known processes as described hereafter.

A convenient process for preparing the 1α-hydroxyvitamin D esters of general structure VI and VIII involves direct C-1 hydroxylation of compounds V or VII using the general procedures of Paaren et al. (Proc. Natl. Acad. Sci. 75, 2080 (1978)). This process is outlined in Process Schematic 2:

an O-acyl substituent, and Z typically represents an alkyl radical such as methyl or ethyl, propyl, etc., although intermediates in which Z is hydrogen or an acyl group (acetyl, benzoyl) are also useful for the subsequent conversion shown in the schematic.

The process involves the tosylation of the hydroxyester V (or VII) to the 3-O-tosyl compound followed by direct solvolysis of this tosylate in an alcoholic solvent (e.g. methanol, ethanol, etc.) containing a suitable buffer such as sodium acetate or sodium bicarbonate to yield the cyclovitamin intermediate 4 (where Z represents an Process Schematic 2

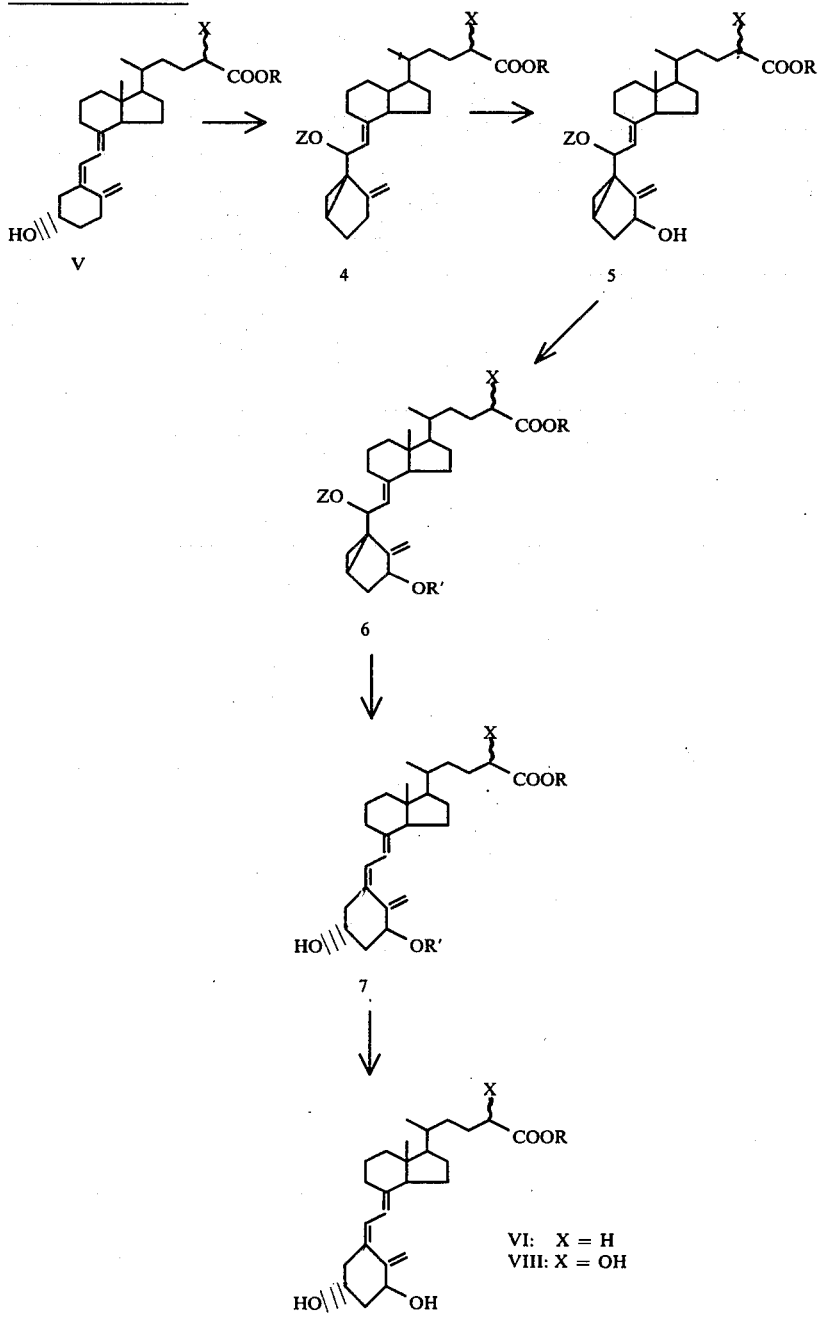

VI: X = H
VIII: X = OH

In the structures of the above process schematic R represents an alkyl radical of about 1 to about 4 carbons, $R^1$ designates an acyl unit such as acetyl or benzoyl, X may be hydrogen or hydroxy, $X^1$ may be hydrogen or alkyl group corresponding to the alkyl residue of the solvent used in the solvolysis reaction, i.e. when methanol is used, Z=methyl, when an aqueous solvent is used Z=H, etc.). Treatment of intermediate 4 with selenium dioxide and hydroperoxide or alkyl hydroperoxide (e.g. t-butyl-hydroperoxide) then yields the 1α-hydroxycyclovitamin D intermediate 5, which is acylated to (6) by standard methods. Solvolysis of compound 6, in formic acid, yields a mixture of 1-O-acyl-vitamin D carboxylic acid ester 3-formate and the corresponding 5,6-trans-isomer. The formyl group is removed by hydrolysis under very mild conditions which does not hydrolyze the ester groups on C-1 or C-25 and the mixture is then fractionated by chromatography (thin-layer or high-pressure liquid chromatography) to yield the pure 1α-O-acyl-intermediate of general structure 7. Subsequent base hydrolysis in alcoholic base removes the acyl group, and gives the desired 1α-hydroxyvitamin D ester of structures VI or VIII. Esters of general structure VI or VIII are new compounds.

An alternative preparation for 1α-hydroxy- compounds VI or VIII from homocholenic acid esters is outlined in process schematic 3, where R represents an alkyl group of 1-4 carbon atoms, X may be hydrogen or hydroxy, $R^1$ is an acyl group such as acetyl or benzoyl, and $X^1$ is hydrogen or O-acyl. This process involves the introduction of a 1α-hydroxy function via an intermediate 1α,2α-epoxy-4,6-dien-3-one steroid (e.g. product 9), following the general procedures of Barton et al. (J. Am. Chem. Soc. 95, 2748 (1973)). Conversion of the resulting 1α-hydroxy-5-ene compound (compounds 10 and 11) to the 5,7-diene (e.g. 12) and subsequent irradiation and thermal isomerization follow the conventional practices already discussed in connection with process schematic 1, to yield the desired 1α-hydroxy compounds VI or VIII.

Process Schematic 3

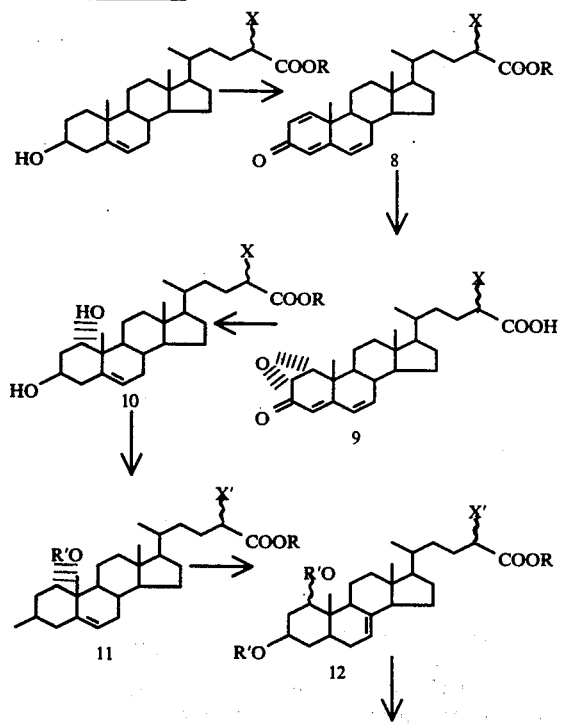

Process Schematic 3
-continued

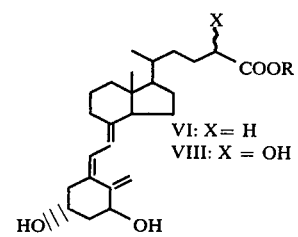

VI: X = H
VIII: X = OH

For the preparation of 24-hydroxyvitamin D esters of general structures VII and VIII by the processes outlined in schematics 1, 2 or 3 above, a 24-hydroxylated homocholenic acid ester is required as the ultimate precursor. Such compounds can be prepared by several methods. One convenient route to 24-hydroxy homocholenic acid esters is illustrated in process schematic 4.

Process Schematic 4

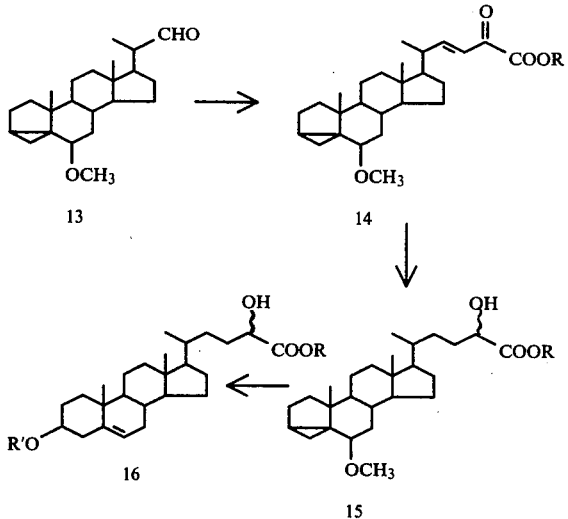

The 22-aldehyde 13, readily available from stigmasterol by the procedure of Partridge et al. (Helv. Chim. Acta 57, 764 (1974)), is condensed (aldol reaction) with pyruvic acid to yield, after esterification, the unsaturated keto ester 14, where R is a hydrocarbon radical of from 1 to about 4 carbons, using, for example, the general procedures of Eyley and Williams (J. Chem. Soc. Perkin Trans. I. p. 727 and 731 (1976)). Treatment of ester 14 with NaBH₄ in pyridine, effects reduction of both the double bond and the keto group and yields the hydroxy ester 15 (see Eyley and Williams, supra). Solvolysis of compound 15, using well-established conditions (see for example Partridge et al supra) yields the 24-hydroxy-homocholenic acid ester 16, where R is a hydrocarbon radical of from 1 to about 4 carbon atoms and $R^1$ may be hydrogen or an acyl group (e.g. acetyl) depending on the solvolysis conditions chosen.

Compound 16 can be readily converted to the 24-hydroxyvitamin D ester VII, by the process shown in Process Schematic 1.

Ester VII can, in turn, serve as the starting material for the preparation of the 1α,24-dihydroxyvitamin D ester VIII, in accordance with the process of Process Schematic 2. Alternatively, compound 16 (with $R^1$=H)

can be converted to 1α,24-dihydroxyester VIII, by the process shown in Process Schematic 3.

C-24-Hydroxylated homocholenic ester analogs can also be conveniently prepared from 24,25-dihydroxycholesterol or from 1α, 24,25-trihydroxycholesterol both of which are known compounds (Lam et al Biochemistry 12, 4851 (1973); Seki et al Chem. Pharm. Bull. (Japan) 21, 2783-2785 (1973); Ikekawa et al, Chem. Pharm. Bull. (Japan) 23, 695-697 (1975)). The conversion of these cholesterol derivatives to 24-hydroxy-homocholenic acid esters or to 1α,24-dihydroxyhomocholenic acid esters is shown in Process Schematic 5.

Process Schematic 5

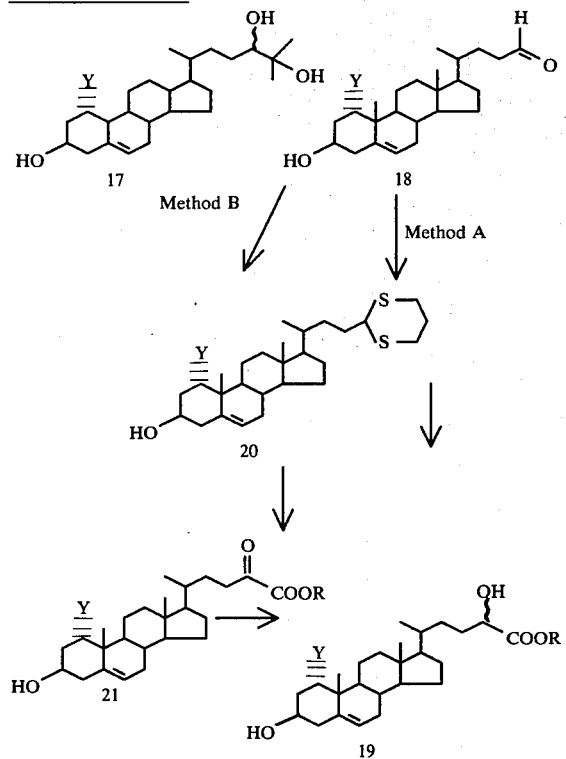

Treatment of a methanol solution of the 24,25-dihydroxycholesterol starting material (17 where Y=hydrogen or hydroxy) with an excess of saturated methanol solution of sodium metaperiodate at room temperature for 2 hours yields the expected cleavage product, the 24-aldehyde (18). This intermediate (after protection of the hydroxy functions as the silyl ethers) can be directly alkylated with 2-lithio-2-methylmercapto-1,3-dithiane (Method A, Process Schematic 5) and the resulting 24-hydroxy-25-orthotrithio ester adduct can be directly converted to the 24-hydroxy-homocholenic acid ester 19 by oxidative alcoholysis of the orthothio ester. (Seebach, Angew. Chem. 79, 469-470 (1969); Seebach, Synthesis p. 17-36 (1969); Ellison et al, J. Org. Chem. 37, 2757 (1972)).

Alternatively (Method B, Process Schematic 5), the 24-aldehyde intermediate 18 can be converted to the 24-thioacetal (20), by treatment with 1,3-propanedithiol in chloroform solution containing BF$_3$-etherate as catalyst. Reaction of compound (20) (after temporary blocking of the hydroxy groups as ether functions, e.g. trimethylsilyl ethers) with n-butyl lithium in tetrahydrofuran solution at low temperature (−20° to −70° C.) under nitrogen or argon atmosphere will generate the 24-lithio derivative which can be directly carboethoxylated by addition of an excess of alkyl chloroformate (e.g. ethyl chloroformate) according to the general procedures of Corey and Seebach (Angewandte Chemie, 77, 1135-1136 (1965)) to give the 24-thioketal 25-carboxylic acid ester intermediate. Treatment of this ester with HgO/HgCl$_2$ in aqueous acetone results in hydrolysis of the thio-ketal with formation of the α-keto ester (21) which can be directly reduced with NaBH$_4$ in methanol to the desired 24-hydroxy-25-homocholenic ester of structure 19 (where R is an alkyl residue of 1-4 carbons, and Y is hydrogen or hydroxy). Ester 19 (with Y=hydrogen) after suitable acylation of the hydroxy groups (e.g. acetylation or benzoylation) can then be converted to 24-hydroxyvitamin D ester VII by the method of Process Schematic 1, whereas ester 19 (with Y=hydroxy) yields the corresponding 1α,25-dihydroxyvitamin D$_3$ ester VIII by the same process.

From vitamin D esters of structure V to VIII the desired 26,27-radiolabeled vitamin D metabolites of structures I-IV can be prepared in a single final step which comprises treating compounds V, VI, VII or VIII with a radiolabeled methyl Grignard reagent (e.g. methyl magnesium bromide or methyl magnesium iodide) or a radiolabeled methyl lithium reagent. The following typical conversions illustrate this final reaction step and the versatality and scope of the process.

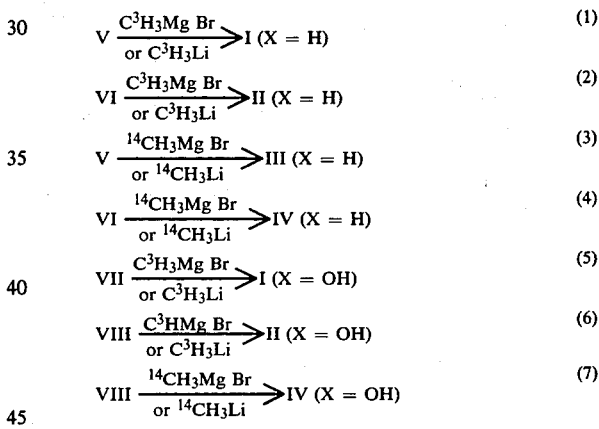

The radiolabeling reactions illustrated by examples (1)-(7) above can be conveniently conducted by reacting an ether solution of the appropriate vitamin D ester (e.g. compounds V-VIII) with an ether solution of the desired radiolabeled Grignard reagent or methyl lithium reagent with ice-bath cooling if during mixing of the reactants, the reaction proceeds too vigorously. The reaction is then conducted at room temperature over a period of about an hour, and the radiolabeled product is then isolated by the standard work-up procedures appropriate for Grignard-type reactions (e.g. addition of H$_2$O or dilute aqueous NH$_4$Cl and ether, separation, washing and drying of the ether phase, followed by evaporation of solvent). Purification of the product using, for example, high pressure liquid chromatography (hplc) on microparticulate silica gel columns, completes the synthesis. It is essential of course, that these operations be conducted in laboratories equipped for the safe handling of radionuclides of high specific activity. The introduction of stable isotopes of carbon and hydrogen ($^{13}$C, $^2$H) is accomplished by the same process using the appropriately labeled methyl-Grignard or methyl lithium reagent, except that no special radiation-safety precautions need to be taken since the stable isotopes present no radiation hazard.

The required radiolabeled reagents are available from suppliers of radiochemicals (e.g. New England Nuclear, Boston, Mass.). Reagents of very high specific activity are available (e.g. $C^3H_3MgBr$ at 80 Ci/mmol). The use of such reagents in the process described above yields, for example, 26,27-tritiated vitamin D metabolites of structure I or II with a specific activity of 160 Ci/mmol. Such levels of radioactivity have not previously been achieved in the vitamin D field, and it would indeed be impossible to prepare compounds of such high specific activity by the radiochemical synthesis heretofore known and employed in this field. The radiosynthesis method described above makes such preparations a matter of routine. Similarly, 26,27-$^{14}$C-labeled metabolites of structures III and IV with specific activities up to 120 mCi/mmol can be prepared by the treatment of compounds V–VIII with the appropriate $^{14}$C-Grignard reagent or methyl lithium reagent. Reagents containing stable isotopes are also commercial products, for example, trideutero methyl iodide and $^{13}$C-methyl iodide are readily available and from these compounds the appropriate Grignard or lithium reagents are easily prepared, as is well-known in the art.

Successful direct treatment of seco-steroids such as compounds V to VIII with radiolabeled Grignard reagents and alkyl metals of high specific activity to yield radiolabeled vitamin D derivatives and analogs is especially noteworth and surprising. The known chemistry of the vitamin D cis-triene chromophore, and of their 3,5-cyclovitamin derivatives demonstrates that these compounds are extremely sensitive to light, oxygen, metal complexation, protic and Lewis acids, and free radicals. They are highly prone to rearrangement, and the available accumulated evidence suggested that treatment of V–VIII with radiolabeled Grignard reagents or alkyl metals of high specific activity would probably cause undesirable and irreversible alteration of the cis-triene system as a result of the chemical nature of the reagents used or the reaction conditions. In addition, the high incident radiation resulting from reagents of high specific activity (for example 80 Ci/mmol for $C^3H_3Mg$ Br) gave rise to the strong possibility that radiolysis by reagents and autoradiolysis of the products would be encountered. There were, therefore, unknown factors that could lead to complications in the syntheses of radiolabeled vitamin D compounds by the methods described herein.

To the present, and although radiolabeled vitamin D metabolites have been necessary and crucial tools for the development of knowledge about the vitamin D endocrine system, and also are essential to each one of the many assays for vitamin D metabolites in blood and tissues of humans and animals, no single, facile method for the convenient introduction of radionuclides has been heretofore found. There is only one example of the use of a Grignard reagent for introduction of tritium (Bell and Scott, J. Label. Compounds 9, 339 (1973)). This example relates, however, to a 1-deoxy-secosteroid with a protected 3-hydroxyl group and the use of $C^3H_3MgBr$ of only modest specific activity (10.6 Ci/mmol). There are no examples of the reaction of high specific activity Grignard reagents or of alkyl metals with esters of 26,27-dinor-vitamin $D_3$-25-carboxylic acid or esters of 1α-hydroxy-26,27-dinor-vitamin $D_3$-carboxylic acid, with or without protection of the A ring hydroxy groups.

There are two reports of radiosyntheses of a vitamin D metabolite with high specific activity (78 and 90 Ci/mmol)(Yamada et al, Anal. Biochem. 85, 34 (1978) and Muccino et al, Steroids 31, 645 (1978)). In both cases the compound was obtained by tritiation of an acetylenic steroid intermediate using $^3H_2$ of high specific activity to introduce the radionuclide, conditions which often result in label scrambling. Both syntheses are difficult and cumbersome requiring seven steps after introduction of the label, including conversion of the steroid to the seco-steroid. Moreover, such processes are not adaptable to labeling the compound with carbon-14, nor could they be used for the preparation of vitamin D compounds with specific activities of greater than 120 Ci/mmol.

The advantages of the processes of this invention are: They are amenable to the introduction of carbon-14, carbon-13, deuterium, and tritium; they do not result in label scrambling; they provide (in the case of radionuclide incorporation) compounds of very high specific activity (up to 160 Ci/mmol); they provide products in which the location of isotope is known unambiguously and in which the isotope cannot be lost by exchange processes (in the case of hydrogen isotopes); they provide introduction of the radionuclide in the last synthetic step and thereby greatly enhance the economy and versatility of the process, and in the case of radionuclides greatly reduce the hazards associated with the synthesis of radiolabeled material.

The flexibility of the new process, in that it allows for the convenient introduction of any isotope of carbon or hydrogen is indeed a noteworthy feature of the present invention. For example, the 26,27-hexadeutero- or 26,27-di$^{13}$C-labeled-vitamin $D_3$ metabolites are readily produced from vitamin D esters of structure V–VIII by treatment with the appropriate deuterated or $^{13}$C-Grignard or methyl lithium reagent. From each of the ester starting materials of type V to VIII one thus has the choice of producing, in a single step, any or all of four isotopically labeled vitamin D compounds: the 26,27-$^3$H-compound, the 26,27-$^{14}$C-compound, the 26,27-$^2$H-compound and the 26,27-$^{13}$C-compound. The preparation of such derivatives by previously known methods would have required four separate multistep syntheses.

Introduction of the isotopic label as the last step offers certain other important practical advantages, because it avoids wasteful loss of material due to low yield conversion. In the preparation of vitamin D compounds from the steroid, the last steps, i.e. formation of the 5,7-diene and the subsequent formation of the seco-steroid by irradiation are both low-yield conversion (e.g. 20-40%). As a consequence, when the label is introduced at the steroid stage, valuable isotope material is lost and expensive reagent is wasted because of these low-yield steps. These losses in turn demand that the labeling process be conducted at relatively large scale (implying the use of large amounts of expensive isotopic reagent which is particularly inconvenient in the case of large amounts of hazardous radioisotope) in order to recover usable quantities of the desired radiolabeled product. Furthermore, the isolation of product from the low-yield reaction steps mentioned above requires careful and difficult chromatography, which is made all the more cumbersome and impractical when applied to highly radioactive compounds. The novel process described herein eliminates all of these problems. A Grignard-type reaction for label introduction is easily conducted (even with highly radioactive reagents) and when the label is introduced as the last step no further chemical manipulations are needed and the isolation of the product requires usually not more than a single chromatographic purification step.

Any process scheme in which radiolabeled is introduced in an early step dictates the preparation of desired radiolabeled product in quantities calculated to meet the expected demand for the product over a long period of time—simply to avoid the necessity of frequent repeats of a difficult and hazardous process. Aside from the many practical problems of multistep processing of large amounts of radionuclides, the requirement for storing the desired products for extended periods, is, of course, another serious disadvantage, since all radiolabeled materials suffer degradation either by natural decay of isotope, which results in loss of specific activity, and/or through radiolysis (particularly for labeled preparations of high specific activity) which can lead to very complex product mixtures. In the present process these difficulties are effectively overcome, since the formation of the radiolabeled product from a stable, conveniently prepared precursor (i.e. compounds V, VI, VII or VIII, which can be stored indefinitely as crystals or in deoxygenated solutions in the cold) in a single, easily repeatable step, offers the option of adapting the amount of radiolabeled product—as well as the nature of the specific isotope introduced—to actual immediate requirements.

The present process is the only method reported to date suitable for the synthesis of tritiated 25-hydroxyvitamin $D_3$ with a specific activity greater than 100 Ci/mmol and it is the first strictly chemical method for the synthesis of the key hormone 1,25-dihydroxyvitamin $D_3$ in radioactive form. The production of vitamin D metabolites in highly radiolabeled form, the use of novel vitamin D esters (compounds V, VI, VII or VIII) as substrates for radiolabeling, together with experimental flexibility, technical simplicity, economy and safety are key features of the present process that distinguish it from prior art.

Although the present specification and the examples refer specifically to the use of vitamin D esters of structures V–VIII, in which the substituent at carbon 24 is hydrogen or hydroxy, for the preparation of 26,27-labeled vitamin D compounds, it should be obvious that vitamin D ester analogs, bearing C-24 substituents such as alkyl, O-alkyl or O-acyl, are equally suitable substrates which, by the isotope-labeling process of this invention, would yield the corresponding 26,27-labeled-vitamin D compounds of structures I–IV in which X is alkyl, O-alkyl and hydroxy, respectively.

Acylated derivatives, or other O-protected derivatives (e.g. O-silyl esters) of vitamin D esters of structure V to VIII are, of course, suitable alternative starting materials for introduction of isotopic label at carbon 26 and 27 by the process of this invention. Such O-protected derivatives are available as intermediates of the preparation of esters V–VIII or are readily prepared from esters V–VIII, by acylation or silylation, and their use for label introduction would represent a self-evident and obvious extension of the isotopic labeling process discussed herein.

It should be noted also that certain intermediates of the syntheses of vitamin D esters V to VIII are also suitable substrates for the introduction of isotopic labels, and such labeled intermediates can subsequently be converted to the labeled vitamin D substances, I–IV. For example, the cyclovitamin D intermediates of structure 5 and 6 in Process Schematic 2, upon treatment with the appropriate radiolabeled Grignard-type reagent, yield the corresponding 26,27-labeled-1α,25-dihydroxy-24-X-cyclovitamin D compound, which by the procedures of Paaren et al, cited earlier, is readily converted to 26,27-labeled-1α,25-dihydroxy-24-X-vitamin $D_3$ (compounds II or IV). Intermediate 4 of Process Schematic 2, treated analogously, yields 26,27-labeled-25-hydroxy-24-X-vitamin $D_3$ (structures I or III). Similarly, the 5,7-diene intermediates of structures 2 or 3 of Process Schematic 1, can be converted to 26,27-labeled-5,7-dienesteroids which after the usual irradiation/thermal isomerization sequence yields any of the compounds I–IV as desired. Because with such intermediates label introduction occurs at a stage further removed from the final product, such modifications of the general process would, in general, not be preferred. They do, however, represent an attractive alternative in certain circumstances. For example, preparation of 26,27-labeled-1α, 25-dihydroxycyclovitamin D compound from intermediates 5 or 6 (Process Schematic 2) might be advantageous if both the 5,6-cis and the corresponding 5,6-trans-26,27-labeled-1α,25-dihydroxy-24-X-vitamin D products are desired, since both are formed upon solvolysis of the cyclovitamin according to the Paaren et al procedures. Similarly the introduction of radio-label into 5,7-diene intermediates (e.g. compounds 3 or 12) would be indicated, if the 26,27-labeled-previtamin D compounds (or 26,27-labeled tachysterol compounds) are desired, since the latter are the immediate products of irradiation of the 5,7-dienes.

In the following examples ultraviolet absorbance (UV) spectra were taken in ethanol with a Beckman Model 24 recording spectrophotometer (Beckman Instruments, Fullerton, Cal.); nuclear magnetic resonance (NMR) spectra were obtained in $CDCl_3$ with a Bruker WH-270 spectrometer (Bruker Instruments, Inc., Wheaton, Ill); mass spectra were obtained at 100° C. above ambient with an AEI (Associated Electrical Industries) MS-9 coupled to a DS-50 data system; high-pressure liquid chromatography (HPLC) was done with a Waters Associates Model ALC/GPC-204 liquid chromatograph (Waters Associates, Milford, Mass.); irradiations were done in a quartz reaction vessel with a 125 watt Hanovia 8A36 lamp fitted with a Corex filter; radioactivity was measured with a Packard Model 3255 liquid scintillation counter (Packard Instrument Company, Inc., Downers Grove, Ill.). Sephadex LH-20 is a hydroxypropyl ether derivative of a polydextran marketed by Pharmacia Chemicals, Piscataway, N.J.; Lipidex 5000 is a 50% saturated hydroxyalkoxypropylation product of Sephadex LH-20 with an average alkoxy group chain length of 15 carbons available from Packard Instruments, Inc., Downers Grove, Ill.; the semi-preparative HPLC column was 0.6×25 cm and was packed with microparticulate silica gel (5 micron particles), preparative-layer chromatography was done on 20×20 cm silica gel plates with a bed thickness of 0.75 or 0.25 cm.

The structural designations in the following examples, by Roman or Arabic numerals, refer to the structures so identified in the preceding specification and the process schematics.

EXAMPLE 1

(a) Preparation of 25-hydroxy(26,27-$^3$H)vitamin $D_3$ (compound I, X=H)

A solution of 1 mg (2.5 μmol) of 26,27-dinorvitamin $D_3$-25-carboxylic acid methyl ester (compound V, R=methyl) in dry ether is treated with an excess of $C^3H_3MgBr$ (80 Ci/mmol) in ether for 1 hr at room temperature (under argon atmosphere). Water is then added to the reaction mixture, the ether layer is separated and the aqueous layer is extracted twice more with ether. The combined ether fractions are washed with water and brine, solvent is evaporated and the residue is purified by chromatography through columns of Sephadex LH-20 (2×50 cm) developed with $CHCl_3$/hexane (1:1) and Lipidex 5000 (1×50 cm) using $CHCl_3$/hexane (1:10), to give 32 mCi of 25-hydroxy-(26,27-$^3$H)vitamin $D_3$ (I, X=H). The product (160 Ci/mmol) thus purified is at least 96% pure, as determined by HPLC. (0.45×25 cm, microparticulate silica gel column, 4% of 2-propanol in hexane as eluting solvent).

(b) Preparation of 25-hydroxy-(26,27-$^2$H$_6$)vitamin $D_3$ (compound I, X=H)

Deuterated methyl-Grignard reagent is prepared by adding $^2H_3$ methyl iodide (60 μmol) in 0.5 ml of dry ether to magnesium turnings (50 μmol). After the metal has dissolved, 2 mg (5 μmol) of 26,27-dinor-vitamin $D_3$-25-carboxylic acid methyl ester (compound V, R=methyl) in 0.5 ml of ether is added, and the reaction is conducted at room temperature for 2 hr. Water and ether are added, the ether phase is separated, and the aqueous phase is extracted twice with ether. Combined organic phases are washed with $H_2O$ and brine and dried over $MgSO_4$ and the solvent is evaporated. Chromatography of the product through Sephadex LH-20 (2×50 cm, $CHCl_3$/hexane 1:1, as solvent) and Lipidex 5000 (1×50 cm, $CHCl_3$/hexane 1:10) gives 25-hydroxy-26,27-hexadeutero vitamin $D_3$. The compound exhibits a maximum of 264 nm in the ultraviolet spectrum and the molecular ion peek at m/e 406 confirms the incorporation of six deuterium atoms.

EXAMPLE 2

(a) Preparation of 1α,25-dihydroxy-(26,27-$^3$H)vitamin $D_3$ (II, X=H)

A large excess of ($^3$H)-methyl magnesium iodide is freshly prepared from ($^3$H)-methyl iodide (80 Ci/mmol) and magnesium powder in dry peroxide-free ether and is added dropwise to a stirred solution of compound VI (R=methyl) in ether under argon. After the addition is complete, the reaction mixture is allowed to stand for 1 hr at ambient temperature. Water is added cautiously and the aqueous phase is extracted several times with ether. The combined ether phases are washed with water and brine. The solvent is removed and the residue is dried by azeotropic distillation of water with benzene. The residue is applied in 10 ml of column solvent to a Sephadex LH-20 column (2×65 cm) and is eluted with chloroform/hexane (13:7). The desired product elutes from 900 to 1100 ml. In HPLC (0.62×25 cm microparticulate silica gel column) developed with 12% 2-propanol/hexane, 1α,25-dihydroxy-(26,27-$^3$H)vitamin $D_3$ (160 Ci/mmol) elutes at approximately 52 ml and is homogeneous. The product shows an ultraviolet absorption maximum at 263 nm; and exhibits a molecular ion at m/e 428 in its mass spectrum, indicative of the incorporation of six tritium atoms.

(b) Preparation of 1α,25-dihydroxy-(26,27-$^2$H$_6$)vitamin $D_3$

To an ether solution of trideutero methyl magnesium iodide prepared as described in Example 1(b) is added 1 mg of 1α-hydroxy-26,27-dinorvitamin $D_3$-25-carboxylic acid methyl ester (compound VI, R=methyl) in 0.5 ml of dry ether. After 1.5 hr at room temperature, water is added to the reaction mixture and the product is isolated by extraction with ether, washing and drying of the ether phases as described in Example 1(b). The product is purified directly by HPLC (0.62×25 cm column of microparticulate silica gel) using 10% 2-propanol in hexane as solvent, to yield the 26,27-hexadeutero analog of 1α,25-dihydroxyvitamin $D_3$ in pure form. ($\lambda_{max}$264 nm; mass spectrum, m/e 422 (M+)).

EXAMPLE 3

Preparation of 26,27-dinorvitamin $D_3$-25-carboxylic acid methyl ester (compound V, R=methyl)

(a) Methyl 3β-hydroxy-25-homo-5,7-choladien-25-oate (3, where X=Y=H and R=methyl)

Methyl 3β-hydroxy-25-homo-5-cholen-25-oate 3-benzoate, 1 ($X^1=Y^1=H$, R=methyl, $R^1$=benzoyl) (0.5 g, 0.99 mmol), sodium bicarbonate (0.55 g, 6.5 mmol), and 1,3-dibromo-5,5-dimethylhydantoin (0.16 g, 0.56 mmol) in hexane 10 ml) are heated under nitrogen for 20 min at 80° C. The reaction mixture is then cooled and filtered. The residue obtained after evaporating the solvent from the filtrate is dissolved in a solution of 2,4,6-trimethylpyridine (1 ml) in xylene (10 ml) and is heated at reflux under nitrogen for 1.5 hr. The reaction mixture is cooled, diluted with benzene, and washed successively with 1 N HCl, dilute $NaHCO_3$, and water. The solvent is removed, and the residue is dissolved in a solution of p-toluenesulfonic acid (0.06 g) in dioxane (12 ml), and heated at 70° C. for 40 min. After cooling the reaction mixture, water and ether are added. The phases are separated, and the organic phase is washed with dilute sodium bicarbonate, water, and brine. The solvent is removed and the residue (compound 2, where $X^1=Y^1=H$, R=methyl, and $R^1$ is benzoyl) is dissolved in a mixture of ether (3.0 ml) and 0.4 M methanolic potassium hydroxide (5 ml). After 2.5 hr at room temperature, water and ether are added, and the organic phase is separated and washed repeatedly with water. The solvent is evaporated and the residue is chromatographed on a silica gel column (1×15 cm) eluted with 25% ethyl acetate/hexane to give the product methyl 3β-hydroxy-25-homo-5,7-choladien-25-oate (3, X=Y=H, R=Me) (0.08 g, 0.2 mmol): UV 294, 282, 272, 264 (shoulder) nm: NMR 0.67 (s, 18-$CH_3$), 1.01 (d, J=6.5 Hz, 21-$CH_3$), 1.04 (s, 19-$CH_3$), 3.72 (s, —$CO_2CH_3$), 5.43, 5.64 (2m, 6H, 7H).

(b) Methyl 3β-hydroxy-25-homo-9,10-secochola-5,7,10(19)-trien-25-oate (26,27-dinorvitamin $D_3$-25-carboxylic acid methyl ester, compound V, R=$CH_3$). A solution of methyl 3β-hydroxy-25-homo-5,7-choladien-25-oate (28 mg) in 20% ethanol/benzene (150 ml), under nitrogen, cooled in an ice bath, is irradiated with UV light for 7.5 min. The solvents are evaporated and the residue is purified by HPLC (10.6×25 cm microparticulate silica gel column developed with 1.5% 2-propanol/hexane) to give starting material (23 mg) and the desired previtamin ester (5 mg); UV $\lambda_{max}$ 260, $\lambda_{min}$ 233 nm, $\lambda_{max}/\lambda_{min}$ 1.5.

The previtamin ester is heated at reflux under nitrogen in ethanol for 4.5 hr to affect double bond isomerization and give the corresponding vitamin ester V (R=CH$_3$): UV $\lambda_{max}$ 264, $\lambda_{min}$ 228, $\lambda_{max}/\lambda_{min}$ 1.8; NMR 0.54 (s, 18-CH$_3$), 0.94 (d, J=6.2 Hz, 21-CH$_3$), 3.67 (s, —CO$_2$CH$_3$), 3.94 (m, 3α-H), 4.82, 5.05 (2 m, 19-H's), 6.03, 6.23 (ABq, J=Hz, 6H, 7H); mass spectrum m/e (relative intensity) 400 (0.85, M+), 382 (0.07 M+-H$_2$O), 369 (0.09, M+ —OCH$_3$), 367 (0.35, M+ —H$_2$O —CH$_3$), 341 (0.10, M+ —CO$_2$CH$_3$), 271 (0.16, M+-side chain), 253 (0.21, M+ —H$_2$O—side chain), 166 (0.31), 158 (0.76), 136 (1.00), 118 (0.91). The compound is homogeneous by HPLC.

EXAMPLE 4

Preparation of 1α-hydroxyvitamin D ester VI (R=CH$_3$) by the cyclovitamin method (a) 6-Methoxy-3,5-cyclo-26,27-dinorvitamin D$_3$-25-carboxylic acid methyl ester (4, X=H, R=Z=methyl)

Methyl 26,27-dinorvitamin D$_3$-25-carboxylic acid methyl ester (V, R=methyl) (25 mg) in dry pyridine (0.3 ml) is treated with p-toluenesulfonyl chloride (50 mg) for 72 hr in the dark at 5° C. The reaction mixture is added to 10% sodium bicarbonate on ice. The aqueous phase is extracted with ether/chloroform (4:1) several times. The combined organic phases are washed with hydrochloric acid, dilute sodium bicarbonate, water, and saturated sodium chloride and dried over magnesium sulfate. Evaporation of the solvent gives the 3-O-tosyl derivative which is one spot on TLC (40% ethyl acetate/hexane, Rf 0.62). The total sample of tosylate is warmed at 55° under nitrogen in a mixture of dry methanol (0.5 ml), sodium bicarbonate, and dichloromethane (0.1 ml). Additional solvent is added as needed to compensate for evaporation. After 11.5 hr, ether and water are added. The phases are separated and the organic phase is washed several times with water and saturated sodium chloride, and dried with magnesium sulfate. TLC shows a major spot with an Rf of 0.42 (20% ethyl acetate/hexane) representing the cyclovitamin ester 4 (R=Z=Me, X=H).

(b)
1α-Hydroxy-6-methoxy-3,5-cyclo-26,27-dinorvitamin D$_3$-25-carboxylic acid methyl ester (5, R=Z=methyl, X=hydrogen)

To selenium dioxide (2.8 mg) in dry dichloromethane (1 ml) at 0° is added t-butyl hydroperoxide (11 μl). The mixture is stirred for 30 min under nitrogen. Cyclovitamin 4 (R=Z=methyl, X=H) in dichloromethane (1.0 ml) is added in one portion. The mixture is stirred for 10 min at 0° and an additional 7 min at ambient temperature, and quenched with saturated sodium bicarbonate. The reaction mixture is extracted with dichloromethane several times and the combined organic phases are washed with water, saturated with sodium chloride and dried with magnesium sulfate. The residue is purified by preparative-layer chromatography (50% ethyl acetate/hexane) to give 1α-hydroxy compound 5 (8.5 mg, Rf 0.35) and the corresponding 1-keto-derivative (5.8 mg, Rf 0.58). Compound 5 (R=Z=Me, X=H) is homogeneous on TLC.

(c)
1α-Acetoxy-6-methoxy-3,5-cyclo-26,27-dinorvitamined D$_3$-25-carboxylic acid methyl ester (6, R=Z=methyl, R$^1$=acetyl, X=hydrogen)

1α-Hydroxy-cyclovitamin 5 (R=Z=Me, X=H) (8.5 mg) and acetic anhydride (0.1 ml) in dry pyridine (0.2 ml) are heated at 55° under nitrogen for 1.5 hr. The reaction mixture is poured onto ice and potassium carbonate is added until effervescence ceases. The mixture is extracted with ether, washed with water, and dried with magnesium sulfate. Evaporation of the solvent gives 8.7 mg of the 1-acetoxy-product (40% ethyl acetate/hexane, Rf 0.55).

(d) Reduction of 1-keto-cyclovitamin

The 1-oxo-cyclovitamin D ester obtained as described in Example 4b, (5.8 mg) is dissolved in tetrahydrofuran (0.6 ml) and methanol (0.1 ml) to which NaBH$_4$ (1 mg) is added. When the reaction is complete (0.5 hr), water and ether are added and the phases are separated. Evarporation of the solvent after work-up affords 1α-hydroxy-cyclovitamin D ester 5 (R=Z=Me, X=H) which is purified by preparative-layer chromatography (50% ethyl acetate/hexane, Rf 0.30).

(e) 1α-Acetoxy-26,27-dinorvitamin D$_3$-25-carboxylic acid methyl ester (7, R=methyl, R$^1$=acetyl, X=hydrogen)

A solution of 1α-acetoxy-6-methoxy-3,5-cyclo-26,27-dinorvitamin D$_3$-25-carboxylic acid methyl ester (prepared as in c above) (8.7 mg) in dry 1,2-dimethoxyethanol (0.3 ml) is treated with formic acid (0.1 ml) at 55° C. under nitrogen for 15 min. The reaction mixture is poured onto ice and sodium bicarbonate is added until effervescence ceases. The product is extracted with ether, washed with water until the aqueous phase has a pH of 6, washed with saturated sodium chloride, and dried with magnesium sulfate. This product (the 3-formate ester) in tetrahydrofuran (0.1 ml) and methanol (0.3 ml) is treated with several drops of saturated sodium bicarbonate for 5 min at ambient temperature. Water and ether are added, and the phases are separated. The ether phase is washed with water, saturated with sodium chloride, and dried with magnesium sulfate. The residue obtained after evaporating the solvent is purified by preparative-layer chromatography. The band with an Rf of 0.2 contains a mixture of 7 (R=Me, R$^1$=acetyl, X=H) and the corresponding 5,6-trans-isomer. The mixture is separated by HPLC (2.5% 2-propanol/hexane, microparticulate silica gel column) with two passes through the column (recycle mode) to give 7 (2.0 mg) and the corresponding 5,6-trans-isomer in pure form.

(f) 1α-Hydroxy-26,27-dinorvitamin D$_3$-25-carboxylic acid methyl ester (VI, R=CH$_3$)

A solution of acetate ester 7 (R=Me, R$^1$=acetyl, X=H) in ether (0.2 ml) is treated with 0.1 M methanolic potassium hydroxide (0.075 ml) at ambient temperature. After approximately 1 hr the reaction is complete. Water and ether are added and the phases are separated. The aqueous phase is extracted with ether. The combined ether extracts are washed with water and saturated sodium chloride solution. Evaporation of the ether gave the desired product VI (R=Me) (1.87 mg) which exhibits one spot on TLC analysis and is homogeneous on HPLC analysis (7.5% 2-propanol/hexane): UV $\lambda_{max}$ 265, $\lambda_{min}$ 228 nm, $\lambda_{max}/\lambda_{min}$ 1.72; NMR δ 0.54 (s, 18-CH$_3$), 0.94 (d, J=6.2 Hz, 21-CH$_3$), 3.63 (s, —CO$_2$CH$_3$), 4.21 (m, 3α-H), 4.40 (m, 1β-H), 4.96, 5.28 (19 E and Z H's), 5.97, 6.32 (AB quartet, J=10.8 Hz, 6 and 7 H's); mass spectrum m/e (composition, m/e calculated, relative intensity) 416.2930 (C$_{26}$H$_{40}$O$_4$, 416.2927, 0.10), 398.2812 (C$_{26}$H$_{38}$O$_3$, 398.2821, 0.09), 380.2694 (C$_{26}$H$_{26}$)$_2$, 380.2716, 0.22), 152.0840 (C$_9$H$_{12}$O$_2$, 152.0837, 0.29), 134.0745 (C$_9$H$_{10}$O, 134.0732, 1.00). The corresponding 5,6-trans isomer, 1α-hydroxy-5,6-trans-26,27-dinorvitamin D$_3$-25-carboxylic acid methyl ester is obtained by hydrolysis of the 5,6-trans-1α-acetoxy compound under the same conditions.

EXAMPLE 5

Preparation of 1α-Hydroxyvitamin D$_3$ ester VI (R=CH$_3$) from homocholenic acid ester (a) Methyl 25-homo-1,4,6-cholatrien-3-on-25-oate (8, R=methyl, X=hydrogen)

A mixture of homocholenic acid methyl ester and 2,3-dichloro-5,6-dicyano-1,4-benzoquinone (3.5 molar excess) in dry dioxane is heated under reflux for 20 to 24 hr. The reaction mixture is cooled and filtered. The residue obtained after evaporation of the solvent is filtered through a neutral alumina column eluted with methylene chloride. The material obtained is purified by chromatography over silica gel eluted with acetone/hexane, and then used as such for the next step.

(b) 1α,2α-oxido-25-homochola-4,6-dien-3-on-25-oic acid (9, X=H)

Trienone 8 obtained as in part a in ether/methanol is hydrolyzed with aqueous potassium hydroxide to convert ester to acid. The cooled mixture is diluted with H$_2$O and extracted with ether to remove organic soluble material. The aqueous phase is then acidified with 1 N hydrochloric acid, and is thoroughly extracted with several portions of ether. The combined organic phases are washed with water and brine and dried over magnesium sulfate. A portion of the residue obtained after evaporation of the solvent equivalent to 3.6 mmol of steroid is dissolved in methanol so that the final concentration of steroid is from 0.05 to 0.1 M. To this solution is added 10% sodium hydroxide (0.45 ml) and 30% H$_2$O$_2$ (2.5 ml), and the resulting mixture is allowed to stand at room temperature for 16 hr. The reaction mixture is acidified with methanolic hydrochloric acid; the solvent is concentrated; and the precipitate representing the desired 1α,2α-epoxy derivative 9 (X=H) is collected and used for the next step.

(c) Methyl 1α,3β-dihydroxy-25-homo-5-cholen-25-oate 1,3-diacetate (11, R=Me, R$^1$=acetyl, X=hydrogen)

Epoxydienone 9 (X=H) (0.25 g) dissolved in dry tetrahydrofuran at −33° C. is added in one portion to a solution of sodium (20-fold excess) in liquid ammonia for a final steroid concentration of 0.015 M. After 10 min ammonium chloride (2.5 g) is added in small portions during 1 hr. The ammonia is allowed to evaporate and 1 N hydrochloric acid and ether are cautiously added to the reaction mixture. The phases are separated and the aqueous phase is repeatedly extracted with ether. The combined organic phases are washed with water and brine and dried over magnesium sulfate. The solution is concentrated and treated with excess diazomethane in ether. The solvent is evaporated and the residue is purified by silica gel chromatography eluted with acetone/hexane to give the 1α-hydroxy-intermediate 10 (X=H, R=methyl).

This 1α-hydroxylated compound is heated (60°) with acetic anhydride/pyridine (1:1) until acetylation is complete (ca. 3 hr, conveniently checked by TLC). The mixture is poured onto ice. Ether is added and potassium carbonate is added until effervescence ceases. The phases are separated and the organic phase is washed with 1 N hydrochloric acid, dilute sodium bicarbonate, water, and brine and dried over sodium sulfate. Evaporation of the solvent provides ester 11 (R=methyl, R$^1$=acetyl, X$^1$=H).

(d) Methyl 1α,3β-dihydroxy-25-homo-5,7-choladien-25-oate 1,3-diacetate (12, R=methyl, R$^1$=acetyl, X$^1$=hydrogen)

Compound 11 (X=H) (1.2 mmol), sodium bicarbonate (500 mg), and 1,3-dibromo-5,5-dimethylhydantoin (0.84 mmol) are heated at 75° under nitrogen for 20 min. The reaction mixture is cooled, filtered, and the solvent is removed. The residue is dissolved in xylene (15 ml) and collidine (3.5 ml) and heated at reflux under nitrogen for 1.5 hr. Benzene is added and the organic phase is washed with 1 N hydrochloric acid, dilute sodium bicarbonate, brine, and dried over sodium sulfate. The residue obtained after evaporation of the solvent is dissolved in dioxane (14 ml) to which p-toluenesulfonic acid (65 mg) is added, and is heated at 70° C. under nitrogen for 35 min. Ether is added, and the organic phase is washed with dilute sodium bicarbonate, water, saturated sodium chloride, and dried over sodium sulfate. The residue obtained after evaporation of the solvent is purified by silica gel thin layer chromatography eluted twice with 10% acetone/hexane, to yield product 12 (R=Me, R$^1$=acetyl, X$^1$=H).

(e) 1α-Hydroxy-26,27-dinorvitamin D$_3$-25-carboxylic acid methyl ester (VI) (R=Me)

A solution of 5,7-diene-diacetate 12 (R$^1$=acetyl, X$^1$=H, R=CH$_3$) (30 mg) in 20% ethanol/benzene (150 ml) under nitrogen at 0° C. is irradiated for 20 min in a quartz reaction vessel with a 125 watt Hanovia 8A36 lamp fitted with a corex filter. The solvent is evaporated and the recovered material is dissolved in ethanol and heated at reflux under nitorgen for 5 hr. The solvent is removed and the residue is dissolved in ether and 0.1 M methanolic potassium hydroxide (2:1) and is allowed to stand at room temperature until hydrolysis is complete (checked by TLC). Water and ether are added and the phases are separated. The aqueous phase is extracted with ether. The combined ether extracts are washed with water and with brine. Evaporation of the solvent yields a product mixture from which the desired Vitamin D ester VI (R=CH$_3$) is separated by HPLC chromatography (0.6×25 cm microparticulate silica gel column) using 7% 2-propanol in hexane as eluting solvent.

EXAMPLE 6

Preparation of 24-hydroxyvitamin D ester VII (R=methyl)

(a) Aldol condensation to keto-ester (14 (R=methyl)

To 20 ml of di-isopropyl amine in 14 ml of dry THF, cooled to 0° C., are added 8.9 ml of n-butyl lithium (1.6 M in hexane); 0.5 ml of pyruvic acid in THF (1.0 ml) is then added dropwise and the solution is stirred at 0° C. for 1 hr. The mixture is cooled to −78° C. and 2.0 g of the 22-aldehyde (13) dissolved in 10 ml dry THF is added. After 1 hr the solution is allowed to warm to 0° C. and then stirred for a further 3 hr. The reaction is quenched with 1 ml glacial acetic acid, diluted with ether and $H_2O$ and the layers separated. The organic phase is washed with 1 N HCl, water and saturated NaCl (aq). The organic layer is dried over anhydrous $Na_2SO_4$ and concentrated in vacuo. The residue is taken up in ether and treated with etheral diazomethane to convert the acid to its methyl ester. The resulting oil is chromatographed over silica gel (100–200 mexh) with 5% ethyl acetate in hexane as eluant to give keto ester 14 (R=methyl).

(b) Reduction of compound 14 to α-hydroxy ester 15 (R=methyl)

To a solution of 1 g of the enone (14) in 30 ml of dry pyridine, 178 mg of $NaBH_4$ is added and the mixture stirred at room temperature for about 48 hr. The mixture is poured into $H_2O$ and extracted with ether. The combined extracts are washed with 1 N HCl, 1 N $NaHCO_3$, saturated NaCl (aq) and dried over anhydrous $Na_2SO_4$. The organic layer is concentrated in vacuo to an oil, chromatographed over silica gel (100–200 mesh) using 5% ethyl acetate in hexane as eluant and 800 mg of α-hydroxy-ester 15 is obtained.

(c) Solvolysis of 15 to 24-hydroxy homocholenic ester 16 (R=methyl, $R^1$=acetyl)

A solution of 648 mg of the compound 15 in 30 ml of glacial acetic acid is warmed to 70° C. for 16 hr. The solution is cooled and neutralized with 10% NaOH (aq) (iced). The solution is then extracted with ether. The combined extracts is washed with 1 N NCl, 1 N $NaHCO_3$, saturated NaCl (aq), dried over anhydrous $Na_2SO_4$ and concentrated in vacuo. The crude solid is chromatographed over silica gel (100–200 mesh) with 5% ethyl acetate/hexane as eluant, to give methyl 3β,24-dihydroxy-25-homo-5-cholen-25-oate 3-acetate (16, where R=methyl, $R^1$=acetyl) in ca. 80% yield.

(d) Conversion of ester 16 to 24-hydroxyvitamin $D_3$ ester VII (R=methyl)

A solution of 500 mg of ester 16 ($R^1$=acetyl, R=methyl) in 3 ml of pyridine is treated with 1 ml of acetic anhydride at room temperature overnight, to yield after the usual work up the corresponding 3,24-diacetate. This material (510 mg) is converted to methyl 3β,24-dihydroxy-25-homo-5,7-choladien-25-oate 3,24-diacetate using the procedure described in Example 3(a). Hydrolysis of the diacetate according to Example 3(a) then leads to methyl 3β,24-dihydroxy-25-homo-5,7-choladien-25-oate (100 mg) which is purified on a short column of silica gel (1×20 cm, 100–200 mesh) eluted with ethyl acetate/hexane (1:4), or by preparative thin layer chromatography (0.75 cm on silica gel plates, ethyl acetate/hexane). Subjecting this 5,7-diene intermediate to the irradiation procedure of Example 3(b) yields the corresponding 24-hydroxy-previtamin D ester which is purified by HPLC (0.6×25 cm, silica gel column, 5% 2-propanol/hexane solvent) and then converted by heating as described in Example 3(b) to the desired 24-hydroxyvitamin D ester VII (where R=methyl). Purity is checked by HPLC and if necessary the product is purified by HPLC using the conditions cited for the purification of the previtamin compound.

EXAMPLE 7

Preparation of ethyl 3β,24-dihydroxy-25-homo-9,10-seco-5,7,10(19)-cholatrien-25-oate (24-hydroxy-26,27-dinorvitamin $D_3$ 25-carboxylic acid ethyl ester (compound VII, R=ethyl) from 24,25-dihydroxycholesterol. (Method A)

(a) 3β-hydroxychol-5-en-24-al (18, Y=H)

To a methanol (10 ml) solution of 1.5 g of 24,25-dihydroxycholesterol (17, Y=H) (prepared as described by Lam et al, Biochemistry 12, 4851 (1973)) is added a saturated methanol solution of sodium metaperiodate. After 2 hours at room temperature, the reaction mixture is diluted with water and extracted with chloroform. The organic extracts are washed with water and brine, dried over potassium carbonate and evaporated to yield ca. 1 g of the desired 24-aldehyde (18, Y=H).

The 24-aldehyde is converted to its 3-O-silyl ether derivative in the usual fashion: reaction of a THF/pyridine (1:1) solution of the aldehyde with hexamethyldisilazane (1.5 ml) and trimethylchlorosilane (1 ml) at room temperature for 0.5 hr. gives the 3-O-trimethylsilyl product, which dissolved in THF is rigorously dried with $K_2CO_3$ and then used as a solution in THF for the next step.

(b) Ethyl 3β,24-dihydroxy-25-homochol-5-en-25-oate (19, Y=H, R=Et)

To a tetrahydrofuran solution of the lithium salt of 2-methylmercapto-1,3-dithiane (prepared as described by Seebach, Angew. Chem. 79, 469–470 (1967); Ellison et al, J. Org. Chem. 37, 2757 (1972)) maintained at −78° under an atmosphere of argon is added dropwise a THF-solution of the 24-aldehyde 3-O-silyl ether (prepared as in (a) above) (ca. 0.8 mole of aldehyde per mole of lithium orthothio-ester reagent). After addition of the aldehyde the mixture is allowed to warm to room temperature and then worked up by addition of water and extraction of the product into $CHCl_3$. The chloroform solution is washed with dilute KOH solution and then water and dried over $Na_2SO_4$. The 24-hydroxy-25-orthothioester intermediate obtained in this manner is then added to a mixture of $HgCl_2$ (3.5 equiv.) and HgO (2.0 equiv.) in 95% ethanol to affect ethanolysis of the orthothioester to the 25-carboxylic ester (Ellison et al supra). The temperature is raised to 50° and the mixture is stirred overnight under argon. Precipitated solids are filtered and washed with $CH_2Cl_2$ and the filtrate is diluted with water extracted with $CH_2Cl_2$, washed with ammonium chloride, sodium bicarbonate, followed by water and brine, drying of the solution ($Na_2SO_4$) and evaporation of solvent gives the desired hydrolysis product ethyl 3β,24-dihydroxy-25-homochl-5-en-25-oate.

(c) Conversion of ethyl
3β,24-dihydroxy-25-homochol-5-en-25-oate to
24-hydroxy-26,27-dinorvitamin D$_3$-25-oic acid ethyl
ester (VIII, R=ethyl), is accomplished by subjecting
ester 19 (Y=H, R=ethyl) to the sequence of steps and
the conditions described in Example 6(d).

EXAMPLE 8

Preparation of ethyl
3β,24-dihydroxy-25-homochol-5-en-25-oate (19, Y=H,
R=ethyl) from 24,25-dihydroxycholesterol (Method B)

(a) Preparation of 24-thioacetal (20, Y=H)

To a chloroform solution of the 24-aldehyde 18 (Y=H) (1 g) prepared as described in Example 7(a) is added an excess of 1,3-dithiopropane (2 ml) and the mixture is stirred at room temperature. Then after ca. 30 min, the mixture is cooled in an ice bath and 1 ml of BF$_3$-etherate is added, and the resulting solution is allowed to stand overnight in the cold. The cold solution is then washed with 5% aqueous KOH solution, followed by washing with H$_2$O and drying over K$_2$CO$_3$. Evaporation of the solvent then yields the desired 24,24-dithioacetal derivative 20, (Y=H). This material is converted to its 3-O-trimethylsilyl ether derivative as described in Example 7(a).

(b) Ethyl
3β-hydroxy-24-oxo-25-homochol-5-en-25-oate (21, Y=H, R=ethyl)

A solution (0.1 M) of the 3-O-silylated-thioacetal derivative obtained as described above in dry tetrahydrofuran maintained at −25° under an atmosphere of argon is treated with 1.5 equivalents of n-butyllithium in hexane (1.5 M solution) and the mixture is stirred for 3.5 hr to yield the desired 24-lithio derivative. The temperature is lowered to −70° and a large excess of ethyl chloroformate (ClCOOEt) is added slowly as a solution in dry THF and the reaction is stirred for 7 hr. It is then allowed to warm to room temperature, water is added, and the mixture is extracted with CHCl$_3$. The CHCl$_3$ extracts are washed with dilute KOH and H$_2$O and then dried and evaporated to yield the 25-carboethoxy-24,24-thioketal derivative. The thioketal is directly hydrolyzed by adding an acetonitrile of solution of the above product (1 mmol) to a solution of excess N-chloro-succinimide (5 mmol) and AgNO$_3$ (4 mmol) in acetonitrile/H$_2$O (5:1). After 1 hr at 50°, saturated NaCl solution is added, the precipitate is removed by filtration and the filtrate after dilution with CH$_2$Cl$_2$ is washed with sodium bisulfite, and sodium bicarbonate solutions followed by water and brine. After drying and evaporation of solvent, the desired 24-keto-25-ethyl ester product (21, Y=H, R=Et) is obtained.

(c) Ethyl 3β,24-dihydroxy-25-homochol-5-en-25-oate
(19, Y=H, R=Et)

A methanol solution (10 ml) of the 24-keto product (100 mg) obtained as in (b) above is treated with excess NaBH$_4$ at room temperature for 45 min. Addition of dilute aqueous acetic acid, and extraction with methylene chloride yields after chromatography on silica gel column developed with ethylacetate/hexane, 85 mg, the desired 24-hydroxy-25-ester product (19, Y=H, R=Et).

EXAMPLE 9

Preparation of 1α,24-dihydroxy-26,27-dinorvitamin
D$_3$-25-carboxylic acid ethyl ester (VIII, R=Et). (Ethyl
1α,3β,24-trihydroxy-25-homo-9,10-seco-5,7,10(19)-cholatrien-25-oate) from
1α,24,25-trihydroxy-cholesterol A methanol solution of 1α,24,25-trihydroxycholesterol is subjected to periodate cleavage exactly as in Example 7(a) to obtain the 1α-hydroxy-24-aldehyde intermediate (18, Y=OH). This aldehyde is converted to its 1,3-ditrimethylsilyl ether using the conditions given in Example 7(a). The silyl ether derivative is then treated with 2-lithio-2-methylmercapto-1,3-dithiane exactly as described in Example 7(b) and the resulting 24-hydroxy-25-ortho-thioester is subjected to ethanolysis using the conditions given in Example 7(b), to obtain ethyl 1α,3β,24-trihydroxy-25-homochol-5-en-25-oate (19, R-ethyl, Y=OH). After acetylation of this triol ester with excess acetic anhydride in pyridine at 80° for 4 hr, the resulting 1,3,24-triacetate is subjected to the procedures given in Examples 5(d) and 5(e) to give the desired product 1α,24-dihydroxy-26,27-dinorvitamin D$_3$-25-carboxylic acid ethyl ester (VIII, R=Ethyl) the only difference being that the final product is purified on HPLC chromatography (0.6×25 cm silica gel column) with 10% 2-propanol in hexane as eluant.

EXAMPLE 10

Preparation of 1α,24-dihydroxy-26,27-dinorvitamin
D$_3$-25-carboxylic acid ethyl ester (VIII, R=Ethyl) via
cyclovitamin intermediates 24-Hydroxy-26,27-dinor-vitamin D$_3$-25-carboxylic acid ethyl ester (VII, R=Ethyl) as obtained by any of the syntheses of Examples 7 or 8 is tosylated at C-3 and then solvolyzed in MeOH/NaOAc exactly as described in Example 4(a) to yield (ca. 40%) 24-hydroxy-6-methoxy-3,5-cyclo-26,27-dinorvitamin D$_3$24-carboxylic acid ethyl ester (compound 4, R=Et, X=OH, Z=Me). Oxidation of this material with SeO$_2$ in the presence of t-butyl-hydroperoxide as detailed in Example 4(b) affords the corresponding 1α-hydroxy-derivative (, R=Et, X=OH, Z=Me) in ca. 50% yield. Acetylation of this product as in Example 4(c) gives the 1,24-diacetate intermediate which is solvolyzed in formic acid exactly as described in Example 4(e) to yield a mixture of the 5,6-cis and 5,6-trans 3-O-formyl vitamin D esters. The formyl groups is directly removed by brief basic hydrolysis exactly as in Example 4(e) and a mixture of 1α,24-diacetoxy-26,27-dinorvitamin D$_3$-25-carboxylic acid ethyl ester and the corresponding 5,6-trans-isomer is obtained. The 5,6-cis and trans isomers are separated on silica gel plates (ethyl acetate/hexane) and HPLC (silica gel column, 0.6×25 cm; 3.5% 2-propanol/hexane) the 5,6-cis isomer (compound 7, R=Et, R$^1$=X$^1$=Acetyl) is hydrolyzed in dilute alkali exactly as in Example 4(f) to give the desired product 1α,24-dihydroxy-26,27-dinorvitamin D$_3$-25-carboxylic acid ethyl ester (VIII, R=Ethyl), in pure form. (Minor impurities, if present, are removed by HPLC chromatography on silica gel (0.6×25 cm column) using 10% 2-propanol/hexane as solvent.) Hydrolysis of the 5,6-trans-1α-acetoxy compound under identical conditions yields 1α,24-dihydroxy-5,6-trans-26,27-dinorvitamin D$_3$-25-carboxylic acid methyl ester.

We claim:
1. Compounds of the structure

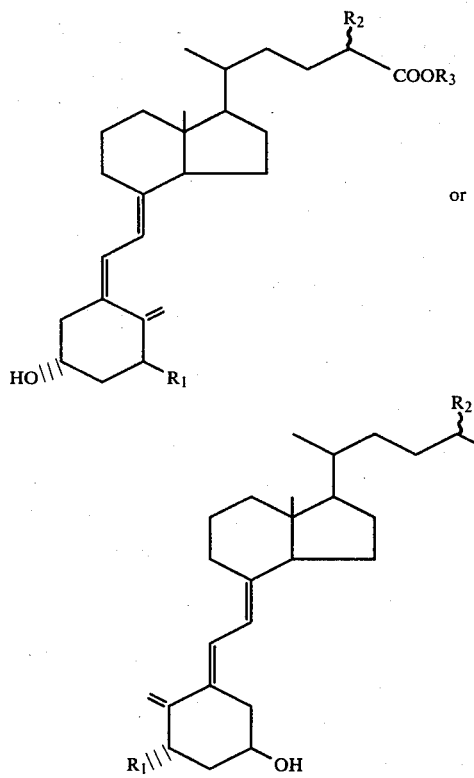

where each of $R_1$ and $R_2$ is selected from the group consisting of hydrogen, and hydroxy with the proviso that $R_1$ and $R_2$ cannot both be hydrogen and $R_3$ is an alkyl group of from 1 to about 4 carbon atoms, and the acylates thereof.

2. The compounds of claim 1 wherein $R_3$ is selected from the group consisting of methyl or ethyl, and $R_4$ is hydrogen.

3. The compounds of claim 1 wherein $R_1$ is hydroxy, $R_2$ is hydrogen and $R_3$ is selected from the group consisting of methyl or ethyl and $R_4$ is hydrogen.

4. The compounds of claim 1 wherein $R_1$ is hydrogen and $R_2$ is hydroxy and $R_3$ is selected from methyl or ethyl and $R_4$ is hydrogen.

5. The compounds of claim 1 wherein both $R_1$ and $R_2$ are hydroxy and $R_3$ is selected from methyl or ethyl and $R_4$ is hydrogen.

6. Compounds of the structure

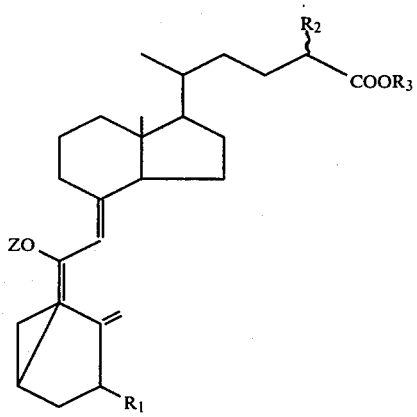

wherein each of $R_1$ and $R_2$ is selected from the group consisting of hydrogen, hydroxy, and O-acyl, and where $R_3$ is an alkyl group of from 1 to about 4 carbon atoms, and where Z is hydrogen or lower alkyl.

7. The compounds of claim 6 wherein both $R_1$ and $R_2$ are hydrogen, $R_3$ is selected from ethyl or methyl, and Z is methyl.

8. The compounds of claim 6 wherein $R_1$ is selected from hydroxy or O-acyl, $R_2$ is hydrogen, $R_3$ is selected from methyl or ethyl, Z is methyl.

9. The compounds of claim 6 wherein $R_1$ is hydrogen, $R_2$ is selected from hydroxy or O-acyl, $R_3$ is selected from methyl or ethyl, Z is methyl.

10. The compounds of claim 6 wherein both $R_1$ and $R_2$ are hydroxy or O-acyl, $R_3$ is selected from methyl or ethyl, and Z is methyl.

11. Compounds of the structure

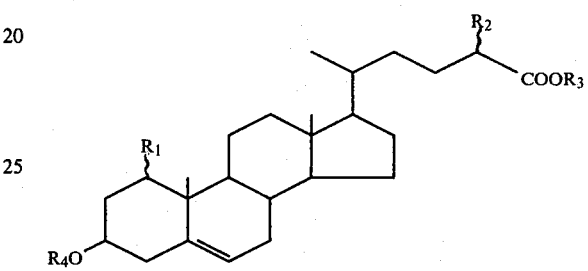

where each of $R_1$ and $R_2$ is selected from the group consisting of hydrogen, hydroxy, and O-acyl with the proviso that $R_1$ and $R_2$ cannot both be hydrogen and $R_3$ is an alkyl group of from 1 to about 4 carbon atoms and $R_4$ is hydrogen or acyl.

12. The compounds of claim 11 wherein $R_1$ is hydroxy, $R_2$ and $R_4$ are both hydrogen, and $R_3$ is selected from methyl or ethyl.

13. The compounds of claim 11 wherein both of $R_1$ and $R_4$ are hydrogen, $R_2$ is hydroxy and $R_3$ is selected from methyl or ethyl.

14. The compounds of claim 11 wherein both of $R_1$ and $R_2$ are hydroxy, $R_3$ is methyl or ethyl, $R_4$ is hydrogen.

15. Compounds of the structure

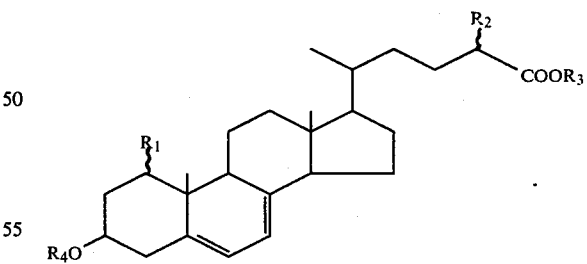

where each of $R_1$ and $R_2$ is selected from the group consisting of hydrogen, hydroxy, O-acyl, except that $R_1$ and $R_2$ cannot both be hydrogen, and where $R_3$ is an alkyl group of from 1 to 4 carbon atoms and where $R_4$ is selected from hydrogen or acyl.

16. The compounds of claim 15 wherein $R_1$ is hydroxy, $R_2$ and $R_4$ are both hydrogen, and $R_3$ is methyl or ethyl.

17. The compounds of claim 15 wherein $R_1$ and $R_4$ are both hydrogen, $R_2$ is hydroxy and $R_3$ is methyl or ethyl.

18. The compounds of claim 15 wherein $R_1$ and $R_2$ are both hydroxy, $R_3$ is methyl or ethyl, and $R_4$ is hydrogen.

19. The compounds of the general structure

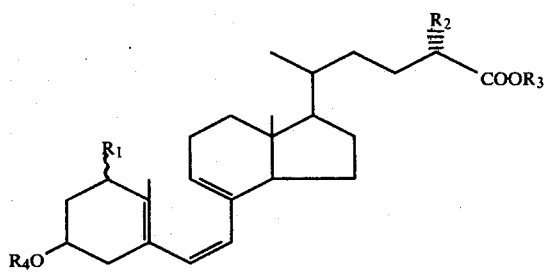

wherein each of $R_1$ and $R_2$ is selected from the group consisting of hydrogen, hydroxyl, and O-acyl, with the proviso that $R_1$ and $R_2$ cannot both be hydrogen, and $R_3$ is an alkyl group of from 1 to about 4 carbon atoms and $R_4$ is hydrogen or acyl.

20. The compounds of claim 19 wherein each of $R_1$ or $R_2$ and $R_4$ is hydrogen, and $R_3$ is selected from methyl or ethyl.

21. The compounds of claim 19 wherein $R_1$ is hydroxy and each of $R_2$ and $R_4$ is hydrogen, and $R_3$ is selected from methyl or ethyl.

22. The compounds of claim 19 wherein both $R_1$ and $R_4$ are hydrogen, $R_2$ is hydroxy, and $R_3$ is selected from methyl or ethyl.

23. The compounds of claim 19, wherein both $R_1$ and $R_2$ are hydroxy, $R_3$ is selected from methyl or ethyl, $R_4$ is hydrogen.

* * * * *

UNITED STATES PATENT OFFICE
CERTIFICATE OF CORRECTION

Patent No. 4,269,777　　　　　　Dated May 26, 1981

Inventor(s) Hector F. DeLuca et al

It is certified that error appears in the above-identified patent and that said Letters Patent are hereby corrected as shown below:

In Column 6, line 46, "Me,uml/u/ llner" should be --Müllner--

In Column 7, Process Schematic 2, formulae 6 and 7,

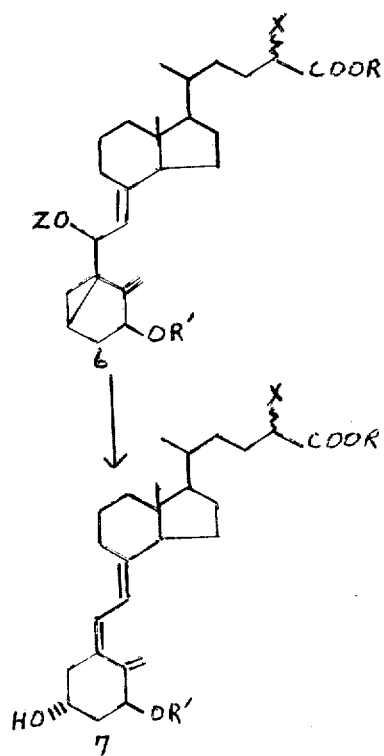

UNITED STATES PATENT OFFICE
CERTIFICATE OF CORRECTION

Patent No. 4,269,777　　　　　　　　　Dated May 26, 1981

Inventor(s) Hector F. DeLuca et al

It is certified that error appears in the above-identified patent and that said Letters Patent are hereby corrected as shown below:

should be

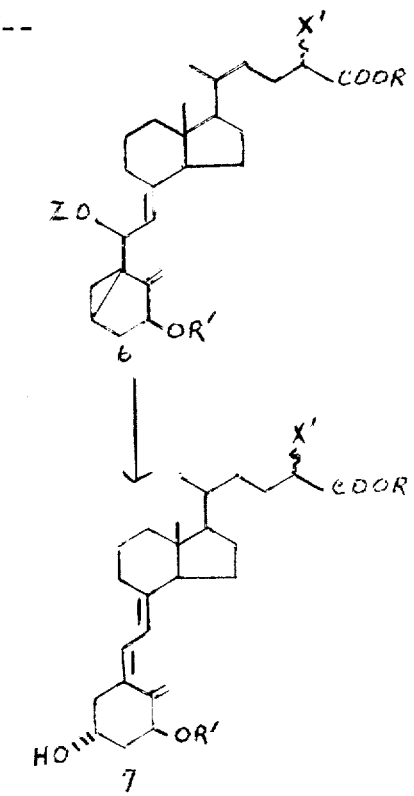

UNITED STATES PATENT OFFICE
CERTIFICATE OF CORRECTION

Patent No. 4,269,777  Dated May 26, 1981

Inventor(s) Hector F. DeLuca et al

It is certified that error appears in the above-identified patent and that said Letters Patent are hereby corrected as shown below:

In Column 9, Process Schematic 3, formula 12,

"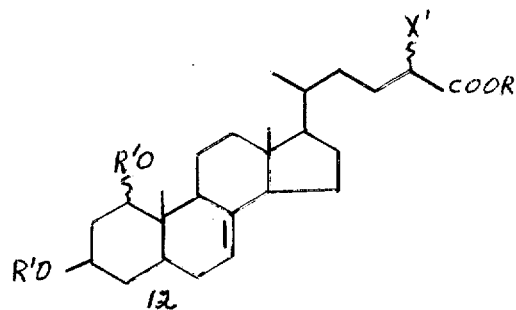"

should be

"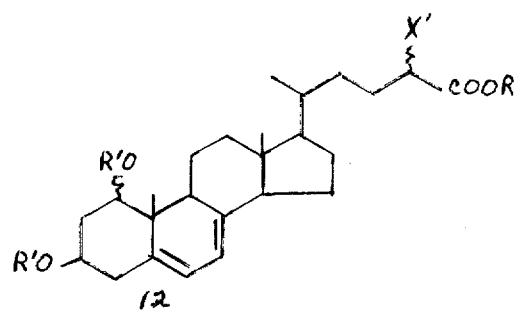"

Signed and Sealed this

Twenty-fifth Day of August 1981

[SEAL]

Attest:

GERALD J. MOSSINGHOFF

Attesting Officer   Commissioner of Patents and Trademarks